(12) United States Patent
Mosharraf et al.

(10) Patent No.: US 11,278,617 B2
(45) Date of Patent: Mar. 22, 2022

(54) IMMUNOGENIC COMPOSITION FORMING A SARS-COV-2 VACCINE, AND A METHOD FOR ITS MANUFACTURE

(71) Applicant: Engimata, Inc., Pleasanton, CA (US)

(72) Inventors: Mitra Mosharraf, Danville, CA (US); Aryo Sorayya, Danville, CA (US); Rajiv Nayar, Danville, CA (US)

(73) Assignee: ENGIMATA, INC, Pleasanton, CA (US)

( * ) Notice: Subject to any disclaimer, the term of this patent is extended or adjusted under 35 U.S.C. 154(b) by 0 days.

(21) Appl. No.: 16/925,438

(22) Filed: Jul. 10, 2020

(65) Prior Publication Data

US 2021/0299251 A1    Sep. 30, 2021

Related U.S. Application Data

(60) Provisional application No. 63/003,254, filed on Mar. 31, 2020.

(51) Int. Cl.

| | | |
|---|---|---|
| *A61K 9/127* | (2006.01) | |
| *A61K 9/19* | (2006.01) | |
| *A61K 9/51* | (2006.01) | |
| *A61K 39/39* | (2006.01) | |
| *A61K 39/215* | (2006.01) | |

(52) U.S. Cl.
CPC ............. *A61K 39/39* (2013.01); *A61K 9/127* (2013.01); *A61K 9/19* (2013.01); *A61K 9/5123* (2013.01); *A61K 39/215* (2013.01)

(58) Field of Classification Search
None
See application file for complete search history.

(56) References Cited

U.S. PATENT DOCUMENTS

| | | | |
|---|---|---|---|
| 9,603,799 B2 * | 3/2017 | Sorayya | ............... A61K 9/0019 |
| 10,494,406 B2 | 12/2019 | Sawada et al. | |
| 10,584,356 B2 | 3/2020 | Ter Meulen et al. | |
| 10,588,963 B2 | 3/2020 | Stegmann et al. | |
| 2019/0359990 A1 | 11/2019 | Tuller et al. | |
| 2020/0009244 A1 | 1/2020 | He et al. | |

FOREIGN PATENT DOCUMENTS

WO    WO-2016138160 A1 *    9/2016    ....... G01N 33/56983

OTHER PUBLICATIONS

He et al., Journal of Virology, 2006, 80(12):5757-5767. (Year: 2006).*
He et al., Journal of Immunology, 2004, 173:4050-4057. (Year: 2004).*

* cited by examiner

*Primary Examiner* — Nicole Kinsey White
(74) *Attorney, Agent, or Firm* — Caldwell Intellectual Property Law; Katherine Rubino

(57) ABSTRACT

An immunogenic composition forming a vaccine includes a nanoparticle adjuvant comprising at least a nanoparticle, wherein the at least a nanoparticle comprises a lipid layer exterior including a plurality of lipids, cholesterol, and a primary alkyl amine including a positively charged amino group head and at least a carbon tail and an antigen incorporated in the at least a nanoparticle, wherein the antigen comprises a spike protein from a coronavirus.

19 Claims, 10 Drawing Sheets

IMMUNOGENIC COMPOSITION FORMING A SARS-COV-2 VACCINE, AND A METHOD FOR ITS MANUFACTURE

CROSS-REFERENCE TO RELATED APPLICATIONS

This application claims the benefit of priority of U.S. Provisional Patent Application Ser. No. 63/003,254, filed on Mar. 31, 2020 and entitled "LIPOSOMAL VACCINE ADJUVANT FOR VIRUS SPIKE PROTEINS AND METHODS OF MAKING AND USING SAME," the entirety of which is incorporated herein by reference.

FIELD OF THE INVENTION

The present invention generally relates to the field of vaccine compositions and methods of making and using the same. In particular, the present invention is directed to an immunogenic composition forming a vaccine, and a method for its manufacture.

BACKGROUND

Coronaviruses are an emerging pandemic threat that humans rarely have innate immunity to. Infection typically results in mild respiratory symptoms but can be more serious in infants and older adults, especially those with underlying comorbidities. Respiratory infection is second only to malaria as a cause of infant mortality worldwide and accounts for substantial hospitalization burden in both age groups in developed countries. Moreover, some pathogens, such as newly emergent zoonotic viral strains, can pose a significant risk of mortality to the general population as well. Despite intensive effort, including numerous vaccine candidates currently in preclinical or clinical development, a safe and effective vaccine for coronaviral infections is still an elusive goal.

SUMMARY OF THE DISCLOSURE

In an aspect, an immunogenic composition forming a vaccine includes a nanoparticle adjuvant comprising at least a nanoparticle, wherein the at least a nanoparticle comprises a lipid layer exterior including a plurality of lipids, cholesterol, and a primary alkyl amine including a positively charged amino group head and at least a carbon tail and an antigen incorporated in the at least a nanoparticle, wherein the antigen comprises a spike protein from a coronavirus.

In another aspect, a method of manufacturing an immunogenic composition forming a vaccine includes forming a nanoparticle adjuvant, wherein the adjuvant comprises a plurality of nanoparticles and each nanoparticle comprises a lipid layer exterior including a plurality of lipids, cholesterol, and a primary alkyl amine including a positively charged amino group head and at least a carbon tail. The method includes providing an antigen, the antigen comprising a plurality of spike proteins from a coronavirus. The method includes combining the antigen with the nanoparticle adjuvant.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

Embodiments disclosed herein present a novel vaccine designed against spike proteins from coronaviruses, such as SARS-CoV-2, using a lipid-based nanoparticle formulation. Formulation may include a liposomal formulation. A resulting vaccine may be scalable, flexible in its antigen presentation, and have the potential for stability outside the cold chain. In an embodiment, a vaccine may include a positively charged chemical vaccine additive for cell targeting, and may include a liposomal vaccine adjuvant with entrapped, embedded, and/or surface adsorbed viral spike proteins and protein complexes of a variety of viruses belonging to the *Coronaviridae* family of viruses for efficient presentation of the viral spike proteins to the immune system. This presentation of the viral spike protein antigen may induce a strong immune response in vivo and lead to the generation of coronavirus-neutralizing antibodies and significant amelioration of infection to coronaviral infections.

Embodiments may include, as a non-limiting example, a liposomal or other lipid-based nanoparticle vaccine formulation that includes entrapped, embedded, and/or surface adsorbed glycoproteins, of a variety of oligomeric states, found on enveloped viruses such as coronaviruses. "Spike proteins" are glycoproteins responsible for binding to host cell surface receptors and subsequent viral entry and represent a preeminent source of potential antibody-recognizing antigens. These spike protein complexes are believed to elicit a protective adaptive immune response in generating neutralizing antibodies against the viral surface, resulting in antibody opsonization and prevention of viral-mediated entry into host cells via spike protein interactions with host cell receptors. A potential avenue to combat such viruses may thus be to create a vaccine against these spike proteins, and other similar glycoproteins, which have been extensively characterized for other human coronavirus such as SARS and MERS, as well as non-human animal coronaviruses such as PEDV, FPIV, and MHV. Presentation of these antigenic glycoproteins in a more physiologically relevant, lipid-associated presentation to the immune cells may be essential to eliciting an appropriate immune response.

The pandemic caused by the Severe Acute Respiratory Syndrome Coronavirus 2 (SARS-CoV-2), previously known as the 2019 novel coronavirus (2019-nCoV) is an example of such an enveloped virus that has a trimeric spike (S) protein at its viral surface. The trimeric S protein of SARS-CoV-2, consisting of an S1 protein and a S2 protein, is responsible for binding to the host cell surface receptor, Angiotensin-converting enzyme 2 (ACE2), and trigger subsequent receptor-mediated viral entry into the host cell. Symptoms in infected patients include fever, coughing, malaise, night sweats, headache, and breathing difficulties that may ultimately be fatal, especially in elderly patients or those with underlying diseases. Currently, there are no effective vaccines against human coronaviruses. Additionally, there are human and non-human coronaviruses with significant health and/or economic impact or potential impact including, without limitation, SARS (Severe Acute Respiratory Syndrome), MERS (Middle Eastern Respiratory Syndrome), MHV (Mouse Hepatitis Virus), PEDV (Porcine Epidemic Diarrheal Virus), and FIPV (Feline Infectious Peritonitis Virus); the last three infect only non-human animals, but boast high mortality rates and rates of infection and attack economically and scientifically important species.

Referring now to FIG. 1, an exemplary embodiment of an immunogenic composition 100 is illustrated. Immunogenic composition 100 includes a nanoparticle adjuvant. An "adjuvant," as used in this disclosure, is a pharmacological and/or immunological agent that improves, or helps to stimulate, an immune response of a vaccine, antigen, or other immunologically active compound. Nanoparticle adjuvant includes at least a nanoparticle 104. A "nanoparticle," as used in this disclosure, is a particle of matter between 1 and 2000 nanometers in diameter. For instance, and without limitation, at least a nanoparticle 104 may be engineered to have an average size less than 500 nm in diameter. At least a nanoparticle 104 may be engineered to have a diameter between 50 nanometers and 2000 nanometers. At least a nanoparticle may have a diameter between 50 nanometers and 1000 nanometers. At least a nanoparticle may have an average diameter of approximately 200-300 nanometers. At least a nanoparticle may include a plurality of particles, a large majority of which are between 80 nanometers and 500 nanometers in diameter; a small number of outliers may be between 5 nanometers and 1200 nanometers. At least a nanoparticle 104 may include a plurality of nanoparticles, which may be suspended, without limitation, in an aqueous medium, lyophilized, and/or cryogenically preserved as described in further detail below. At least a nanoparticle 104 includes a lipid layer 108 exterior including a plurality of lipids, which may vary in physicochemical properties. Lipid layer 108 exterior may include, without limitation, a lipid monolayer, bilayer, and/or multi-lamellar construction and/or lipid corona about a non-liposome nanoparticle, which may include any nanoparticle as described above, or the like. At least a nanoparticle 104 may include, for instance, a liposome. A "liposome," as used in this disclosure, is a vesicle enclosed by a lipid and/or phospholipid bilayer. Alternatively or additionally, at least a nanoparticle 104 may include a micelle, defined as a lipid monolayer enclosure, a bicelle, an amphipol, a nanodisc, a styrene-maleic acid lipid particle (SMALP), and/or a nanostructure such as a piece of inorganic and/or organic material such as metal-based, metal oxide, carbon-based, immune-stimulating complex (ISCOM), protein cages, or other nanoparticles with a lipid material, or the like. Lipid and/or lipids making up lipid layer 108 and/or nanoparticle 104 construction may include, without limitation, phospholipids such as dipalmitoyl phosphatidylcholine (DPPC), dioleoyl phosphatidylcholine (DOPC), non-phospholipid lipids incorporating and/or combined with polyethylene glycols (PEGs), such as without limitation, PEGylated lipids, PEG-conjugated lipids, or the like, zwitterionic, neutral, cationic, and/or anionic phospholipids and non-phospholipids such as phosphatidylcholine, ceramides, phosphatidylethanolamine, saturated, monounsaturated and/or polyunsaturated fatty acid lipids, and the like. Lipids may be selected from the FDA GRAS list for approved excipients, for instance to guard against any biosafety issues. Lipid layer 108 includes cholesterol 112 and/or cholesterol 112 derivatives, including cholesterol with other functional groups added on; cholesterol derivatives may include, without limitation, cholesterol derivatives denoted as disterol-phospholipid Bis-Azo-PC, Chol-T, Chol-Q, or the like. Lipid layer 108 includes a primary alkyl amine 116, defined as a structure having an amine functional group and one or more carbon tails in an unbranched and/or branched carbon chains formation; primary alkyl amine 116 may include without limitation nonadecanamine, stearylamine, heptadecylamine, cetylamine, tripentyalmine, and/or isomers of the alkyl amines, or the like.

Primary alkyl amine 116 includes a positively charged amino group head and at least a carbon tail. Non-limiting examples of primary alkyl amine 116 include stearylamine (SA), pentylamine ($C_5H_{13N}$), alkyl amines of any carbon length, as well as branched alkyl amines such as tripentyalmine, amylamines, or the like, mixtures of isomers of the above, and/or alkyl amines with varying degrees of poly- and mono-unsaturated carbon chains, such as alkene and/or alkyne substituted alkyl amines. Primary alkyl amine 116 may be positively charged. As a result, lipid layer 108 and/or at least a nanoparticle 104 may be positively charged; in an embodiment, positive charge of primary alkyl amine 116 may neutralize a net negative charge of at least a nanoparticle 104 and/or may cause overall charge of at least a nanoparticle 104 to become positive. In an embodiment, and without limitation, where at least a nanoparticle 104 is positively charged, at least a nanoparticle 104 may attract spike proteins having negative charges, improving entrapment and/or adsorption to lipid surface of spike protein. In a non-limiting example, a positive charge of combined nanoparticle and antigen may further have an effect of attraction to negatively charged cell membranes of immune and/or somatic cells, which may cause combined nanoparticle and antigen to contact and/or deliver into such cells the antigens; this may increase immunogenic effect of the resulting vaccine by improving cell-targeting. In some embodiments, spike proteins may alternatively or additionally complex bind to lipid layer; for in instance, spike protein may interact and change protein conformation to effect a complex bind, which may occur as a non-limiting example where a formulated vaccine is lyophilized and then reconstituted. In some embodiments, where antigen has a positive charge, alkyl amine and/or an additional compound having a negative charge, such as without limitation DPPG (dipatmityl, dioleoyl, disterylphosphatidylglycerol), alginate, and/or polyalginate, may be used to give lipid layer a net negative charge. Generally, where antigen has an electric charge with a first polarity, lipid layer exterior may have an electric charge with a second polarity, wherein the first polarity differs from the second polarity; i.e. a where the first polarity is negative the second polarity may be positive, and vice-versa.

Figure 1:
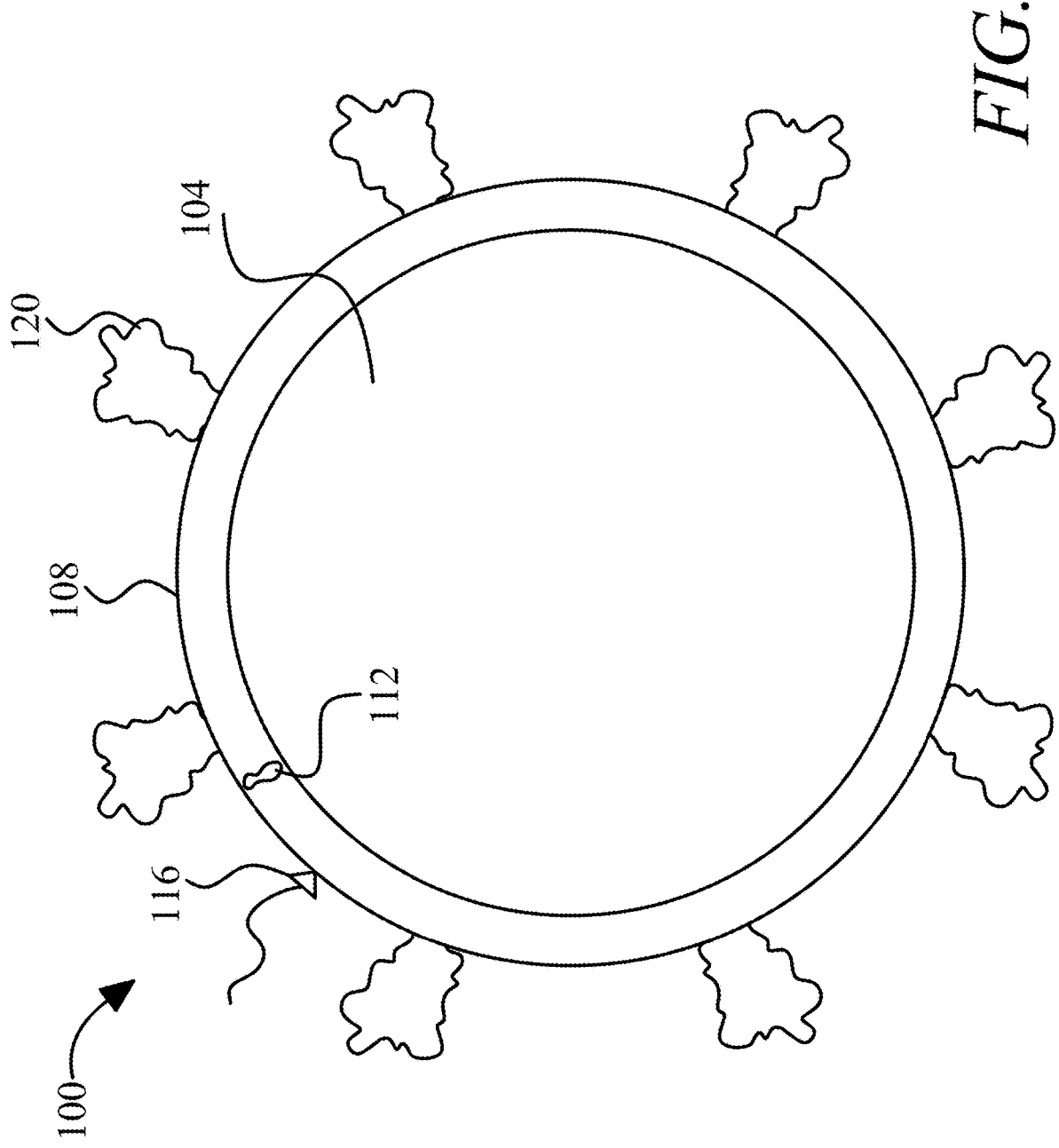
FIG. 1 is a schematic diagram of an exemplary embodiment of an immunogenic composition.

Still referring to FIG. 1, as a non-limiting example, materials used in lipid layer 108 and/or liposome may include cholesterol 112 at approximately 20 mol %, saturated lipids DPPC in an amount of approximately 40 mol %, SA, positively charged, at approximately 15 mol %, and unsaturated lipid DOPC neutral, at approximately 25 mol %. In a non-limiting, illustrative embodiment, ratios of lipids may be in a range of DPPC:DOPC:cholesterol 112:alkyl amine molar ratio is 40:20-30:20:10-30. In an embodiment, differing molar ratios may be used to optimize various recombinant forms of spike proteins, and/or improve adsorption of coronavirus spike proteins from other species.

Further referring to FIG. 1, immunogenic composition 100 includes an antigen incorporated in the at least a nanoparticle 104. An "antigen," as used in this disclosure, is a viral molecule and/or molecular structure that may induce an antigen-specific antibody response and/or result in immune cell antigen receptor-binding. In an embodiment, antigen includes a spike protein from a coronavirus, which may include any virus in the subfamily *Orthocoronavirinae*. A "spike protein," as used in this description, is a protein and/or glycoprotein structure that projects from, lies, on, or traverses a surface of a virus particle. A spike protein in a coronavirus may be referred to as an "S" protein, for instance S1 or S2. Spike protein may include without limitation a trimeric protein complex or one or more subunits thereof, such as an S1 subunit, an S2 subunit, or the like, or homo- and/or hetero-oligomeric forms of these proteins. In an embodiment, and as described in further detail below, an S2 subunit may be embedded in a lipid bilayer of a virus particle, while a corresponding S1 subunit may bind to the S2 protein and project beyond the bilayer, extending away from the virus particle surface to engage host cells; this may enable a coronavirus to penetrate such cells by binding, for instance, the human ACE2 receptor, leading to internalization of the virus particle and/or a payload thereof, and ultimately infection. Spike protein, and/or any sub-unit thereof as described above may contain at least a post-translational modification (PTM) such as glycosylation, phosphorylation, acetylation, ubiquitination, isoprenoid attachment, or the like. Spike protein may be recombinant, and/or may be harvested from partial and/or whole viral particles. For instance, and without limitation, spike protein may include NCP-CoV (2019-nCoV) spike protein (S1+S2 ECD) and/or SARS-CoV-2 (2019-n-Cov) Spike S1-His recombinant protein. Spike protein may include a His tag; in such an example, a 'His tag' may be a poly-histidine amino acid fusion tag, as part of a recombinant spike protein, used for purification of the recombinant spike protein. Recombinant spike protein forms may contain purification tags, artifacts, or the like, including histidine tags, maltose-binding protein (MBP) tags, streptavidin-biotin tags, FLAG tags, and the like. Recombinant spike proteins and/or any viral glycoproteins used in nanoparticle formulations may originate from prokaryotic and/or eukaryotic recombinant expression systems, for instance and without limitation, mammalian cell expression, bacterial cells expression, yeast cell expression, and insect cell-baculoviral expression systems, and the like. Recombinant spike proteins and/or viral glycoproteins may be modified in DNA sequence to optimize recombinant expression and/or purification, but still result in faithfully recapitulated amino acid sequences resembling native viral proteins. Spike protein may be HPLC-verified. Persons skilled in the art, after reviewing the disclosure in its entirety, will be aware of the various forms purified recombinant viral proteins may present.

With continued reference to FIG. 1, a spike protein or other antigen may include, without limitation, a glycoprotein. A glycoprotein is a surface-exposed viral structural protein that contains glycans—carbohydrate PTMs on the surface and/or within the protein. An S1 glycoprotein of a coronavirus may be, without limitation a homotrimer, a monomer, and/or a dimer. A process whereby glycans are chemically modified onto a surface of a glycoprotein is referred to as the process of "glycosylation," and is a post-translational modification (PTM) defined as a chemical attachment to a protein after synthesis in the cell. Glycosylation may function to shield, or otherwise alter, antigenic sites on a virus for immune cell avoidance. Different glycosylation states may exist for glycoproteins such as SARS-CoV-2 glycoproteins, including without limitation other PTMs such as hydroxylation, methylation, lipidation, acetylation, disulfide bond formation, ubiquitination, SUMOylation, phosphorylation, proteolysis, and the like, as described above. Depending on the recombinant source, there may be final glycosylation states that differ in their modification pattern, amount, branching, and physicochemical properties, and potentially their immunogenicity; for instance, different forms of glycosylation may result from recombinant production of spike proteins in insect, mammalian, bacterial, and yeast cells or other organisms used for recombinant manufacture of the spike protein. In some embodiments, spike proteins used may evince varying truncated and/or mutated forms such as forms having various amino acid mutations.

Further referring to FIG. 1, in alternative embodiments, antigen may include one or more surface proteins of other types of viruses, such as without limitation influenza virus or respiratory syncytial virus (RSV). Antigen may alternatively or additionally include surface proteins besides spike proteins, such as "M" proteins; in an embodiment, use of a mixture of S proteins and M proteins may modify and/or improve overall immunogenicity, stability, glycoprotein packing, or the like.

Figure 3:
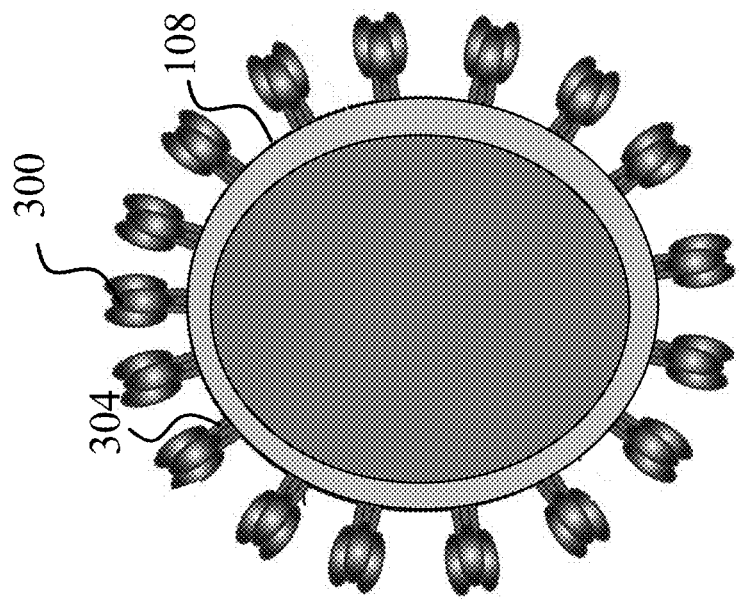
FIG. 3 is a schematic diagram of an exemplary embodiment of an immunogenic composition.
Figure 2:
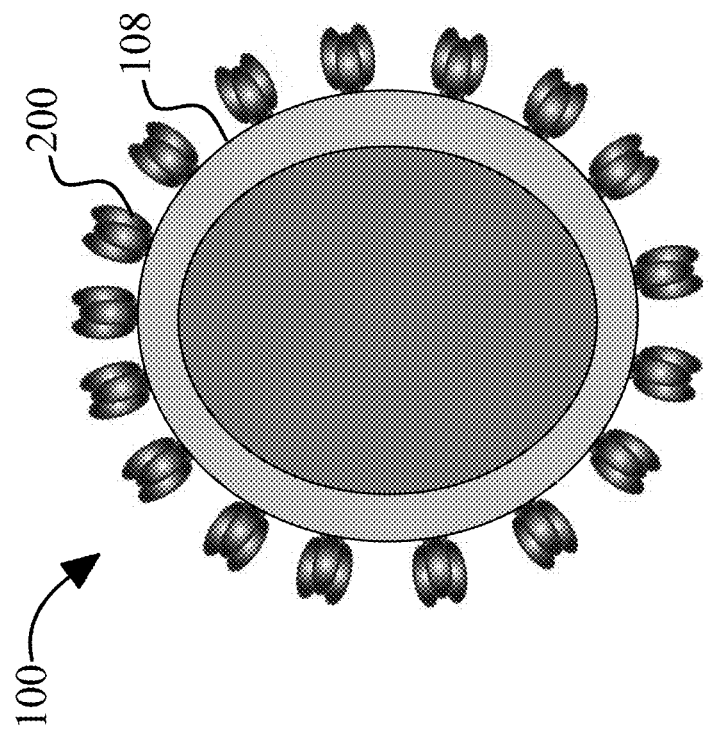
FIG. 2 is a schematic diagram of an exemplary embodiment of an immunogenic composition.
Figure 4:
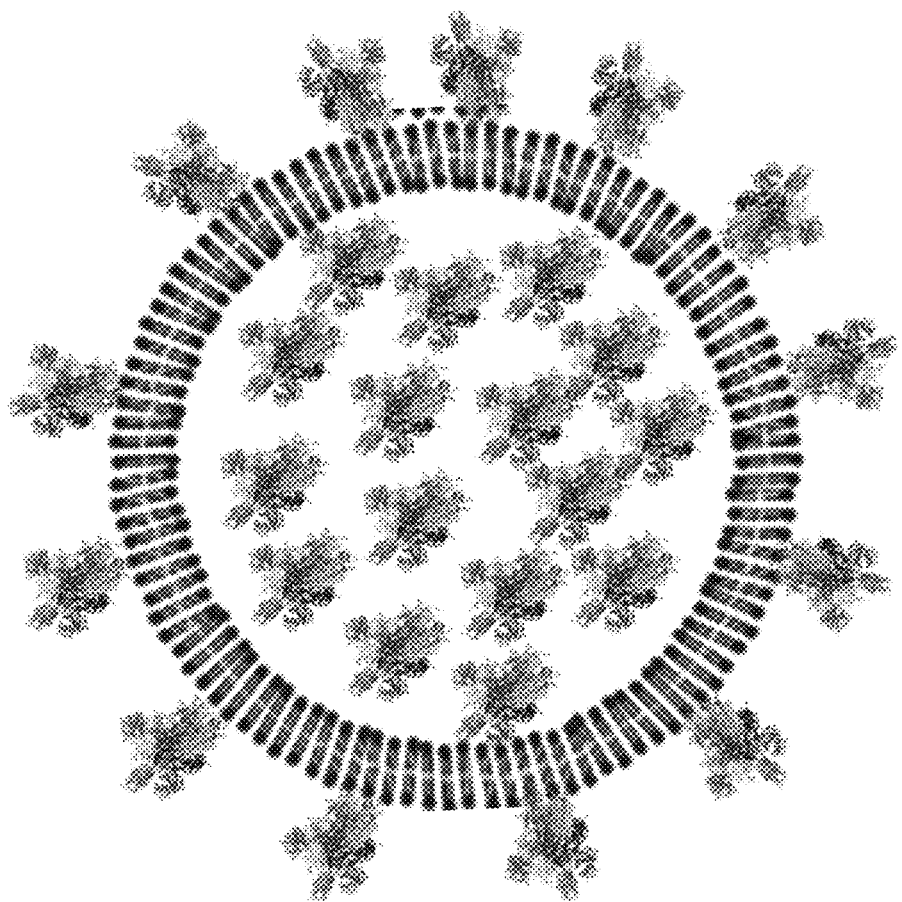
FIG. 4 is a schematic diagram of an exemplary embodiment of an immunogenic composition.

Still referring to FIG. 1, antigen is incorporated in the at least a nanoparticle 104. "Incorporation," as used herein, is any form of attachment, adsorption, and/or entrapment on or in a nanoparticle; for instance, and without limitation, antigen may be adsorbed to a surface of lipid layer 108. As a non-limiting example, and as shown in FIG. 2, spike protein may include an S1 protein 200 without an S2 in complex with it, which may be attached to and/or adsorbed to lipid layer. As a further non-limiting example, and as illustrated in FIG. 3, spike protein may include an S2 protein 300 embedded in lipid layer 108, adsorbed to lipid layer 108 and/or bilayer, and/or interacting with lipid layer 108 and/or bilayer, and an S1 protein 304 projecting from the lipid layer 108. As a further non-limiting example, and as shown in FIG. 4, where nanoparticle includes or is a liposome, spike protein may be entrapped in an aqueous compartment of the liposome, and/or may be adsorbed to lipid layer as well. Incorporation may include entrapment between layers of a bilayer; for instance, where lipid layer 108 includes a bilayer and/or multi-lamellar construction, spike protein may be entrapped within the bilayer.

With continued reference to FIG. 1, incorporation may be achieved by optimizing, or otherwise altering, the lipid composition, surface charge of the liposome, and size of the liposomes, as well as any other physicochemical property. For example, a spike protein such as an S1S2 spike protein of SARS-CoV-2 may be a negatively charged protein, for instance with acidic patches, that binds more efficiently to positively charged lipid surfaces and/or liposomes through favorable ionic interactions. Therefore, mixing a positively charged nanoparticle such as a positively charged liposome with an S1S2 spike protein of SARS-CoV-2 may result in protein adsorption to the liposome and/or nanoparticle surface as well as some entrapment inside the liposome and/or nanoparticle. This particle-protein complex may subsequently interact with the immune cells and elicit a protective immune response in generating antibodies to the S1S2 spike protein. Such a protocol may be used for other antigenic proteins in generating a liposomal vaccine. Adsorption may be achieved, without limitation through ionic, hydrophobic, Van der Waals interactions, hydrogen bonding, and/or through covalent interactions and/or conjugation. Methods of manufacture as described in further detail below may entrap the target antigen inside a liposome as well as decorating the liposome surface with spike proteins by adsorption through molecular interactions. Where at least a nanoparticle 104 includes a liposome, liposome composition may be chemically modified to an appropriate surface charge that maximizes binding of target antigen to surface of the liposome and for presentation of the liposomes to the immune cells.

Further referring to FIG. 4, immunogenic composition may be manufactured, stored, and/or prepared in one or more lyophilized forms and/or in one or more dried states using various drying technologies such as without limitation spray drying, vacuum drying, foam drying, or the like. For instance, and without limitation, immunogenic composition and/or one or more components thereof may be presented in an on-demand format in which composition is lyophilized for stability, then reconstituted for use. For instance, and without limitation, immunogenic composition may be formulated as a lyophilized composition, after incorporation of antigen in at least a nanoparticle 104. Alternatively or additionally, nanoparticle adjuvant may be lyophilized separately and reconstituted with the antigen; in other words, incorporation may be performed concurrently with reconstitution. Reconstitution may refer to resuspension, hydration, solvation, or otherwise reconstituted in aqueous solution, including buffer compositions such as phospho-buffered saline (PBS), or the like. In further non-limiting illustrative embodiments, reconstitution of a lyophilized nanoparticle, such as a liposome-glycoprotein complex, may be performed with varying salt concentrations, such as sodium chloride. In an embodiment, reconstitution of separately lyophilized nanoparticles with antigen may cause antigen to be trapped within a vesicle and/or other interior such as an aqueous interior of a liposome as well as attached to a surface thereof.

Still referring to FIG. 4, immunogenic composition 100 may include at least one lyoprotectant. A lyoprotectant, as used in this disclosure, is a substance that protects a substance during cryogenic freezing, during freeze-drying, and/or during freeze-thaw cycles. At least one lyoprotectant may include, without limitation, a polyol, such as without limitation sucrose, trehalose, mannitol, or the like, and/or at least one ionic strength balancing component, including for instance a salt, pH buffer, or the like. At least one lyoprotectant may include an amino acid, such as without limitation glycine, arginine, or the like. Persons skilled in the art, upon reviewing the entirety of this disclosure, will be aware of various alternative or additional lyoprotectants, cryoprotectants, and the like that may be employed consistently with this disclosure.

Still referring to FIG. 4, immunogenic composition 100 may include any suitable combination of elements including without limitation any set of formulations as set forth below in table 1. Formulations may include without limitation protectants such as sugar, pH control buffers, preservatives such as polysorbate 20%, and/or an ingredient such as NaCL or other salts to balance ionic strength.

TABLE 1

Exemplary Formulations

| Vaccine | S1 | S1-S2 | Lipid$^a$ | pH | Buffer | Polysorbate 20% | Sugar |
|---|---|---|---|---|---|---|---|
| B-S1 | 10 µg/mL | — | 25 mg/mL | 7.2 | Histidine | 0.05 | 10% Sucrose |
| B-S1S2 | — | 10 µg/mL | 25 mg/mL | 7.2 | Histidine | 0.05 | 10% Sucrose |

$^a$including cholesterol 112 and alkyl amine.

Still referring to FIG. 4, vaccine may be administered in any suitable manner. In an embodiment, vaccine may be injectable. Vaccine may alternatively or additionally be absorbed through a mucous membrane, for instance via aerosolized delivery to the nostrils and/or lungs. Alternatively or additionally, vaccine may be administered using a patch, such as without limitation a microneedle patch that delivers lyophilized vaccine in powder form; as a non-limiting example, lyophilized vaccine may be included in soluble microneedles which upon insertion to tissue of a living organism may dissolve in fluids thereof, reconstituting and activating the vaccine. As a further non-limiting example, lyophilized vaccine may be delivered in an implant such as a soluble or insoluble needle inserted under the skin or into other tissue allowing fluids of the subject tissue to reconstitute and disseminate the vaccine. Vaccine may be delivered in liquid and/or lyophilized form to any mucous membrane; for instance and without limitation, vaccine may be delivered as a lyophilized inhalable powder for absorption in nasal and/or pulmonary surfaces. Vaccine may be delivered orally, for instance in a needle or other device for injecting lyophilized vaccine into and/or across digestive tissues, which may be delivered in a capsule designed to disintegrate in one or more digestive juices. Vaccine in lyophilized form may be delivered by a nanobot.

Figure 5:
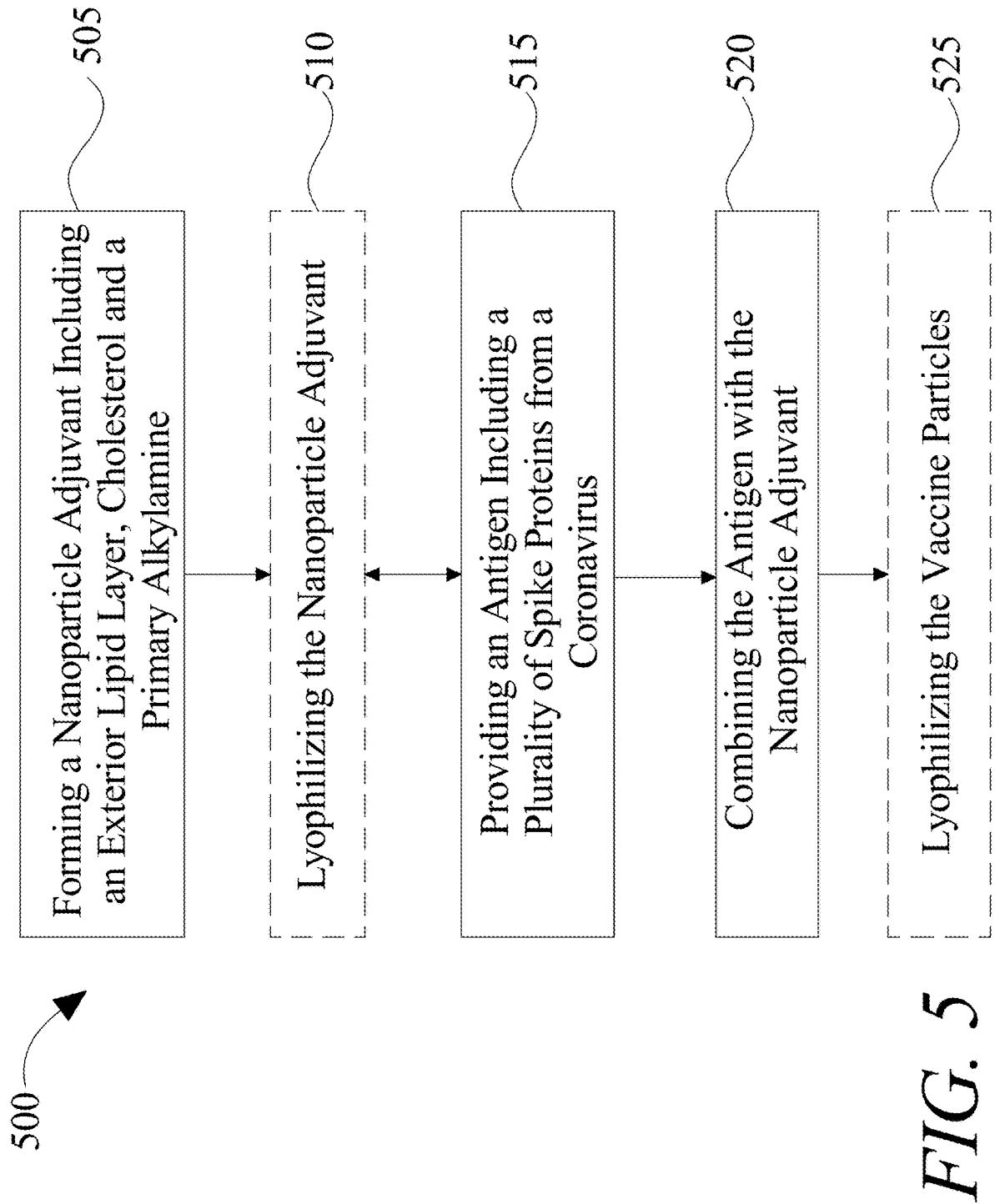
FIG. 5 is a flow diagram illustrating an exemplary embodiment of a method for manufacture of an immunogenic composition.

Referring now to FIG. 5, an exemplary embodiment of a method 500 of manufacturing an immunogenic composition forming a vaccine is illustrated. At step 505, a nanoparticle adjuvant is formed. Nanoparticle adjuvant may include any nanoparticle adjuvant as described above. Nanoparticle adjuvant includes a plurality of nanoparticles, which may include any nanoparticles as described above. Each nanoparticle includes a lipid layer 108 exterior including a plurality of lipids, cholesterol 112, and a primary alkyl amine 116 including a positively charged amino group head and at least a carbon tail, for instance and without limitation as described above. Lipid layer 108 may be positively charged, for instance by application of a concentration of a positively charged alkyl amine as described above. Each nanoparticle may include, without limitation, a liposome.

Still referring to FIG. 5, formation of nanoparticle adjuvant may include formation of a suspension of liposomes. Formation may include hydrating a dried lipid blend, such as without limitation a freeze-dried lipid blend, and extruding the resulting solution through a filter having pore sizes at approximately an upper limit of a desired liposome diameter, which may be a desired diameter falling into ranges and/or average sizes as described above.

At optional step 510, combining may include lyophilizing the nanoparticle adjuvant, for instance and without limitation as described in further detail below.

At step 515, and still referring to FIG. 5, method 500 includes providing an antigen. Antigen includes a plurality of spike proteins from a coronavirus, as described above. For instance, and without limitation, spike protein may include an S1 protein. Spike protein may include an S1S2 protein. Intact spike protein and/or various specific domains, such as S1 and S2 subunits may be recombinant; for instance, and without limitation, intact spike protein and/or specific domains and/or subunits may be manufactured using mammalian cell-culture based expression systems, or a plurality of expression systems as described above. Alternatively or additionally, whole and/or partial virus particles may be generated and/or replicated, and spike proteins and/or subunits may be extracted, separated from, sheared off, or otherwise purified from such whole or partial virus particles, or virus-like particles.

With continued reference to FIG. 5, spike protein may include a glycoprotein. Glycosylation of spike protein may occur during production and/or replication of virus particles. Glycosylation may be varied across batches and/or populations of spike proteins or among individual spike proteins; this may generate a recombinant glycoprotein library with glycoproteins of varying degrees of glycosylation. In an embodiment, spike proteins of varying glycosylation may be combined in the antigen; this may result in nanoparticles, such as liposomes, incorporating a plurality of different glycoproteins of the same species. In an embodiment, such liposomes may allow for greater immunogenicity. For instance, and without limitation, preparation of S1 may include reconstituting S1 in water for injection (WFI) to generate a given concentration, including without limitation a 250 μg/mL S1 stock solution. Specific amounts of S1 stock solution may then be diluted in specific amounts of a formulation buffer, which may include without limitation a 0.01% polysorbate 20/sucrose/histidine buffer to a concentration of approximately 10 μg/mL S1. As a further non-limiting example, a 550 μg/mL S1S2 stock solution, which may be reconstituted without limitation as described above, may be diluted in specific amount of formulation buffer, including any buffer as described above, to a concentration of approximately 10 g/mL S1S2. Buffer may generally include any buffer offering a buffering capacity within a pH range of 6.0-7.5, including without limitation histidine and/or phosphate buffer. Buffer may include a polysorbate 20 or 80 concentration within a range of 0.001%-0.05%. Buffer may include a polysorbate 20 or 80 concentration within a range of 0.001%-0.05%.

At step 520, and still referring to FIG. 5, antigen is combined with nanoparticle adjuvant. In an embodiment, a suspension of protein antigen may be added to an aqueous suspension of nanoparticle adjuvant, using a mixing device to get a homogeneously distributed antigen-liposome mixture. Mixing device may include, without limitation, a magnetic stirrer, a sonication device, a homogenizer, or the like. Mixture may alternatively or additionally be swirled mechanically or manually. Combination according to this technique may tend to produce surface-mounted spike proteins and/or spike proteins adsorbed to lipid surface, for instance as described above. Where nanoparticles have a charge with an opposite polarity to a charge of antigen, antigen may adsorb to the liposomes rapidly. In an embodiment, lyophilized nanoparticle adjuvant may be reconstituted using a suspension of antigen in a buffer solution.

Alternatively or additionally, and continuing to refer to FIG. 5, hydration of lipid blend prior to extrusion may be performed with a solution and/or suspension of antigens; in other words, generation of nanoparticle adjuvant may be performed concurrently with and/or subsequently to combination of antigen with nanoparticle adjuvant. This may produce liposomes that include both entrapped and adsorbed antigens.

At step 525, and still referring to FIG. 5, vaccine particles formed according to any process as described above may be lyophilized. Lyophilized vaccine particles may be delivered and/or stored in lyophilized form and may subsequently be reconstituted prior to administration and/or may be administered in powdered and/or lyophilized form as described above.

Referring now to FIG. 6, a flow diagram illustrating an exemplary embodiment of a method 600 of manufacturing an immunogenic composition forming a vaccine is illustrated. At step 605, an antigen is provided; antigen may include, without limitation, any antigen described above, including without limitation spike proteins and/or glycoproteins of a coronavirus, and/or portions thereof. For instance, and without limitation, antigen may include S1 glycoproteins and/or S1S2 glycoproteins. Provision of antigen may be performed, without limitation, according to any process described above in reference to FIG. 5.

At step 610, and still referring to FIG. 6, a dry lipid blend may be provided and/or formed. As a non-limiting example, a blend of DPPC, DOPC, cholesterol and stearylamine (40:25:20:15:mol %, respectively may be dissolved in a chloroform/methanol/water solution. Solution may be dried, for instance in a rotary evaporator under a stream of nitrogen gas. Solution may subsequently be dissolved in a co-solvent of cyclohexane/80% tertiary-Butyl alcohol (v/v) at a final lipid concentration of 20 mg/ml, for instance in aliquots of 50 mg of lipid/vial. Vials may then be lyophilized to obtain a dried lipid blend; vials may be sealed with nitrogen (N2) gas prior to partial placement of a stopper. Vials may then be freeze dried under a blanket of N2 gas, for instance in a freeze-dryer. As a non-limiting example lipid-blend may be lyophilized by freezing at −45° C., primary drying at −30 to −35 C, and secondary drying at 25-30° C.

Further referring to FIG. 6, lipid blend may be hydrated with an antigen solution and/or suspension, as illustrated at step 615. Antigen solution may include, without limitation antigen combined with a buffer to form a suspension. Buffer may include, without limitation, a lyoprotectant, which may include any lyoprotectant described above. As a non-limiting example, a 200 gr 10 mM histidine, 10% sucrose buffer may be prepared. A pH of buffer may be adjusted to approximately 7.2 when measured at 25 degrees Celsius.

Buffer may be sterile filtered through a filter such as without limitation a 0.2 µm or 0.22 µm filter. Buffer may then be combined with the antigen mixture; alternatively or additionally, combination with antigen may occur concurrently with or subsequent to reconstitution of lyophilized nanoparticles with buffer. For instance, and without limitation, lyophilized lipid-blend may be hydrated with filtered antigen buffer solution and vortexed and/or sonicated until lipids are hydrated and liposomes are formed. Hydration with antigen solution may form a colloidal vaccine solution. At step 620, colloidal vaccine solution may be extruded, for instance using filtration as described above in reference to FIG. 5, to form desired particle sizes. As a non-limiting example, where positively charged dried lipid-blends as described above, may be hydrated with a specific amount of a corresponding spike protein solution such as without limitation a 40 µg/mL spike protein solution; pH of spike protein solution may match pH of lipid and/or nanoparticle solution. A resulting combined solution may be extruded through filters; for instance, a vaccine particle solution may be extruded through a membrane filter, such as through 2×400 nm membrane filters in an extruder such as a 10 mL extruder. As a further non-limiting example, solution may be extruded ten times through two 400 nm polycarbonate filters in a 10 ml extruder at 50-100 psi using nitrogen gas. Extrusion may be performed gradually, for instance in a laminar flow hood using N2 gas. This procedure may be repeated one or more times; extrusion may be repeated until all solution has passed through the extruder 10 times. A resulting solution may be dispensed in vials; for instance, solution may be dispensed in 3 mL depyrogenated glass vials, for instance filling 800 µL fill volume. Dispensation may be performed in a laminar flow hood. Dispensation may be performed using a fine 1 mL pipette and sterile disposable pipette tips. Preparation according to steps 615 and 620 may be referred to herein as formulation "C"; for instance, where antigen is a solution of S1 spike proteins, formulation may be referred to as CS1, while where antigen is a solution of S1S2 spike proteins, formulation may be referred to as CS1S2.

Figure 6:
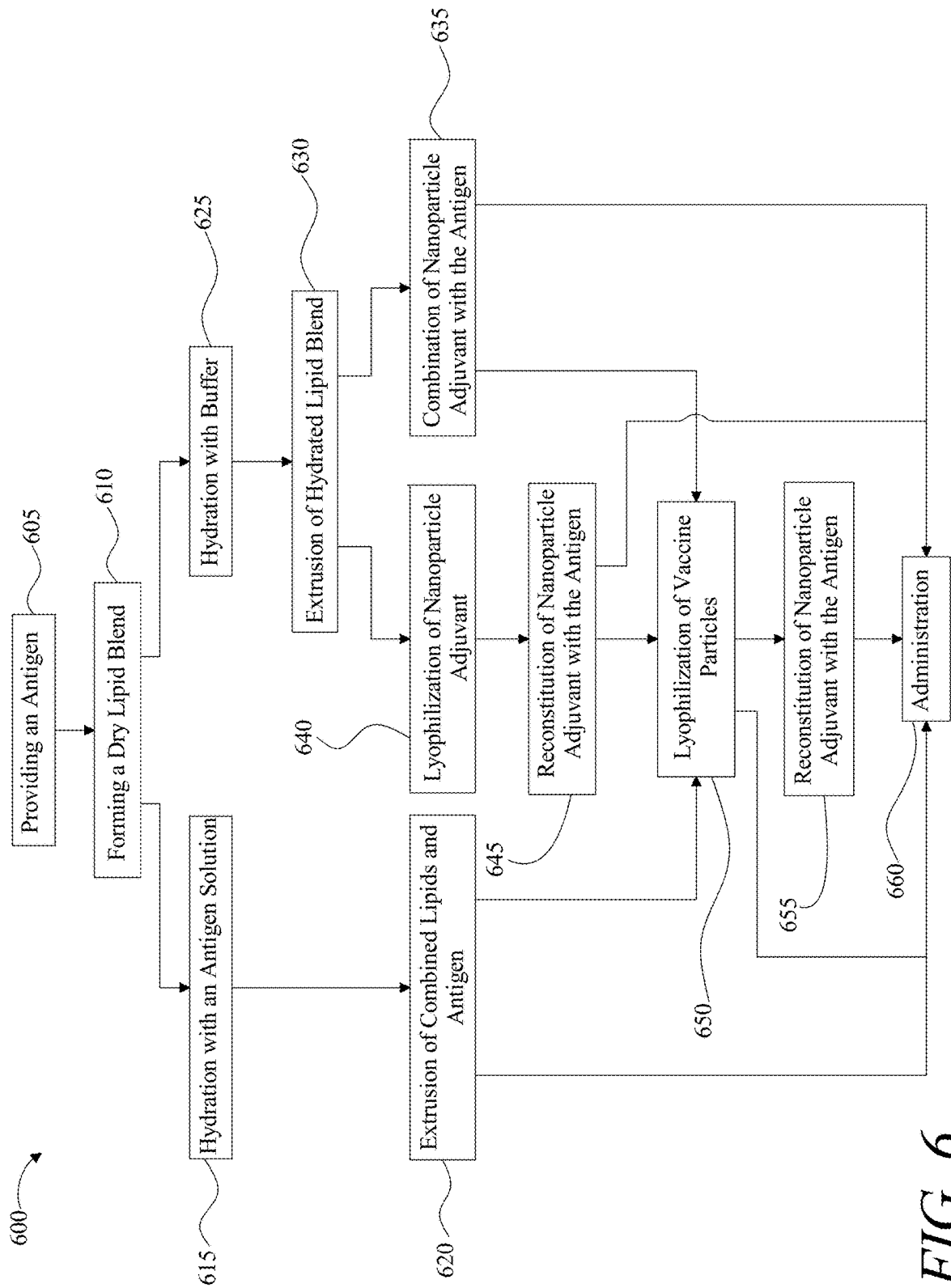
FIG. 6 is a flow diagram illustrating an exemplary embodiment of a method for manufacture of an immunogenic composition.

Alternatively or additionally, and still referring to FIG. 6, at step 625 dried lipid blend may be hydrated with formulation buffer, for instance and without limitation as described above, without antigen to form nanoparticle adjuvant alone as a colloidal solution. For instance, and without limitation, lyophilized lipid-blend may be hydrated with filtered buffer, vortexed and/or sonicated until lipids are hydrated and liposomes are formed. Nanoparticle adjuvant may be extruded and/or dispensed in vials as described above, as illustrated at step 630.

In some embodiments, and with continued reference to FIG. 6, nanoparticle adjuvant as formed at steps 625 and 630 may be combined in its form as a colloidal solution with antigen, for instance by mixing a protein solution of antigen with the colloidal solution of nanoparticles, as illustrated at step 635; this may be implemented, without limitation, as described above in reference to FIG. 5. A formulation as described in reference to steps 625, 630, and 635 is referred to herein as formulation "A"; for instance, where antigen is a solution of S1 spike proteins, formulation may be referred to as AS1, while where antigen is a solution of S1S2 spike proteins, formulation may be referred to as AS1S2.

Alternatively or additionally, and still referring to FIG. 6, nanoparticle adjuvant may be lyophilized, as illustrated at step 640. At step 645, lyophilized nanoparticle adjuvant may be reconstituted with antigen, for instance and without limitation using antigen in a buffered solution. A formulation as described in reference to steps 625, 640, and 645 is referred to herein as formulation "B"; for instance, where antigen is a solution of S1 spike proteins, formulation may be referred to as BS1, while where antigen is a solution of S1S2 spike proteins, formulation may be referred to as BS1S2. In an embodiment, reconstitution of freeze-dried nanoparticles ("B") with spike protein antigens to be trapped within a vesicle such as an aqueous interior of a liposome, as well as adsorbed to and/or trapped in lipid layer 108, for instance as illustrated above in reference to FIG. 4. In an embodiment, mixture of lyophilized adjuvant with antigen may be performed shortly before administration; in other words, lyophilized adjuvant and antigen may be transported and/or stored separately and combined at or near a site of administration.

At step 650, and still referring to FIG. 6, any vaccine formulation described above may be lyophilized. Lyophilized vaccines may be denoted as formulation "D"; for instance, where antigen is a solution of S1 spike proteins, formulation may be referred to as DS1, while where antigen is a solution of S1S2 spike proteins, formulation may be referred to as DS1S2. At least one lyoprotectant as described above may be included with combination of antigen with nanoparticle adjuvant. Lyophilization and/or inclusion of lyoprotectants may be accomplished in any manner consistent with descriptions provided above. For instance, and without limitation vaccines may be filled in vials and freeze-dried in a freeze-drier such as a Vertis Genesis 12XL by first freezing the solution to −45° C. at 0.5° C./min, followed by a 2-hour hold. Further continuing the example, primary drying may be performed below the primary glass transition of the frozen solution (Tg'), for example at −35° C. shelf temperature for at least 10 hours at a chamber pressure of 100 mTorr or until completion of primary drying. After primary drying, and still continuing the example, a shelf may be ramped up to 25° C. at 0.2° C./min. Still continuing the example, secondary drying may be performed at 25° C. shelf temperature for 4 hours at a chamber pressure of 100 mTorr. Second lyophilization of combined proteins and liposomes may cause a complex interaction between antigen, such as S1 or S1S2, and lipids and/or sugar and/or other lyoprotectant. At step 655, freeze-dried vaccines, such as freeze-dried S1 and S1S2 liposomal vaccines (referred to here as D-S1 and D-S1S2) may be reconstituted with water for injection (WFI). A resulting liposome solution may include a 25 mg/mL liposome (or between 1 and 50 mg/mL) and 10 ug/mL S1 or S1S2. Alternatively, lyophilized vaccine may be directly administered.

At step 660, vaccine may be administered, according to any suitable process for administration, including without limitation any process described in this disclosure. The above-described methods are provided for exemplary purposes only; any combination of method steps as described in this disclosure is considered within the scope of this disclosure.

Reference is now made to immunization study results regarding study of immunization to coronavirus in mice. Study was conducted according to an approved Animal Care and Use Protocol (ACUP). 2×50 µl of each formulation tested was injected intramuscularly (im) in the leg of five female BALB-C mice on days 0 and 14. Serum was collected from the immunized mice as well as naïve mice (negative control; non-vaccine injected) on Days 14 and 28. Five mice were tested per group.

An antibody response to each vaccine was determined using an Indirect Enzyme-Linked Immunosorbent Assay (ELISA) method that was designed for the detection of mouse antibodies against SARS-CoV-2 spike proteins. Each microtiter plate (Coster 3369, EIA/RIA Plate) was coated with 0.1 µg of S1 per well or 0.2 µg of S1/S2 per well; testing indicated that use of 0.1 µg of S1/S2 produced similar results. Sera from mice were diluted 100-fold in blocking buffer (0.5% Bovine albumin serum (BSA) in 0.05% Polysorbate 20-20). The diluted sera were serially diluted in duplicate to a final dilution of 6,400 times the initial sera. The plates were incubated at 5° C. overnight (16-18 hours). After washing the plates, horseradish peroxidase-conjugated Goat anti-mouse IgG secondary Antibody (HRP), Sino Biological) was diluted (1 µL/10 mL) in blocking buffer and 100 ul was added to each well to detect the antibodies against spike protein. After a 1-2-hour incubation at 37° C., the plates were washed and tetramethylbenzidine (TMB) substrate was added to detect Ab responses. The reaction was stopped after approximately 5 minutes with 1 N HCl. Immediately, absorbance was measured at 450 nm using a Spectromax 190 microplate reader (Molecular Devices, CA). Endpoint titer for each mouse was determined as the highest dilution of immune serum producing ELISA values ($A_{450}$ nm) greater than or equal to five times the binding detected with a corresponding dilution of naïve mice sera. The mean $A_{450}$ values obtained for the antibodies were calculated for each group of mice per vaccine. In all cases the results are the mean value of IgG titer absorbance for five mice. Samples were stored at 5 C, 25 C, and 40 C up to one month for stability evaluation. Stability was assessed by measurement of particle size and UV absorbance. Freeze-dried vaccine was found to be stable for at least two weeks at 40 degrees C., and one month at 25 degrees; as a result, vaccine may be suitable for transport and storage without refrigeration.

All samples were analyzed on a Precision Detector Dynamic Light Scattering (DLS) instrument PD2000DLS$^{plus}$ and PDDLS/CoolBatch 90T using quartz cuvettes (Precision Detectors). Liposomal samples were diluted 197 times in histidine sucrose buffer, from an original 25 mg/ml suspension. Measurements were done at 20° C. using a refractive index of 1.3479 and a viscosity of 0.0133 Poise for a 10% sucrose solution. Sample time was 15 µsec with a 3 sec run duration and a total of 60 accumulations per measurement. Data was analyzed using Precision Deconvolve software. Stock solutions of S1 and S1S2 (at 250 and 550 µg/mL, respectively) and also 10 µg/mL solutions of S1 and S1S2 were also analyzed without dilution. Particle size was found to be stable between samples.

Figures 7, 8:
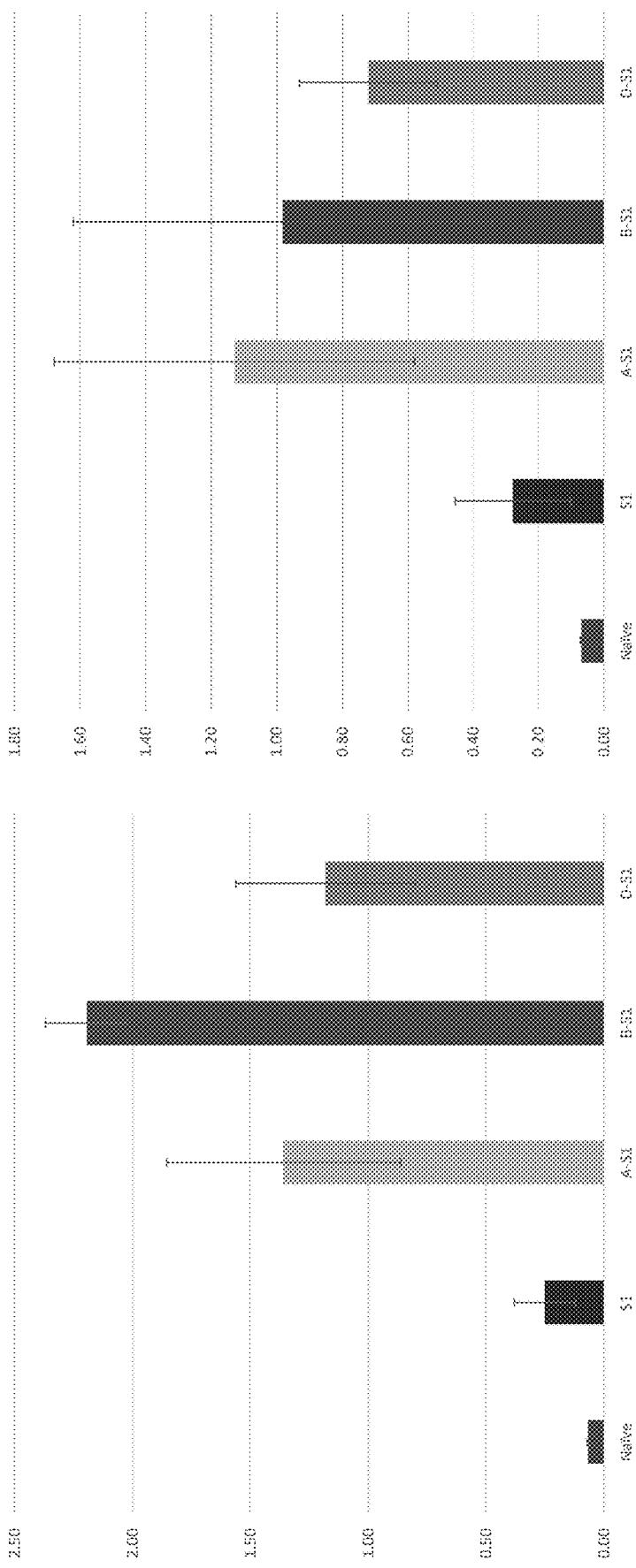
FIG. 7 is a bar graph illustrating experimental results describing relative immunogenicity.
FIG. 8 is a bar graph illustrating experimental results describing relative immunogenicity.
Figures 9, 10:
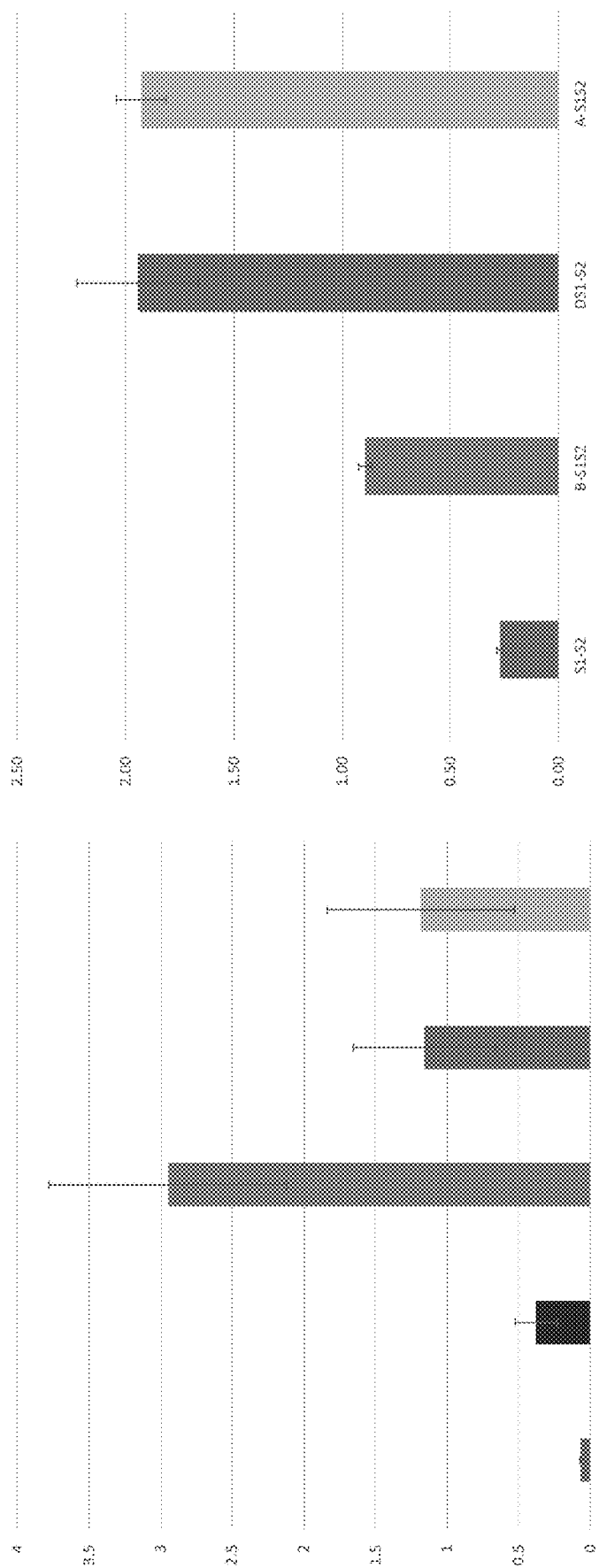
FIG. 9 is a bar graph illustrating experimental results describing relative immunogenicity.
FIG. 10 is a bar graph illustrating experimental results describing relative immunogenicity.
Figure 11:
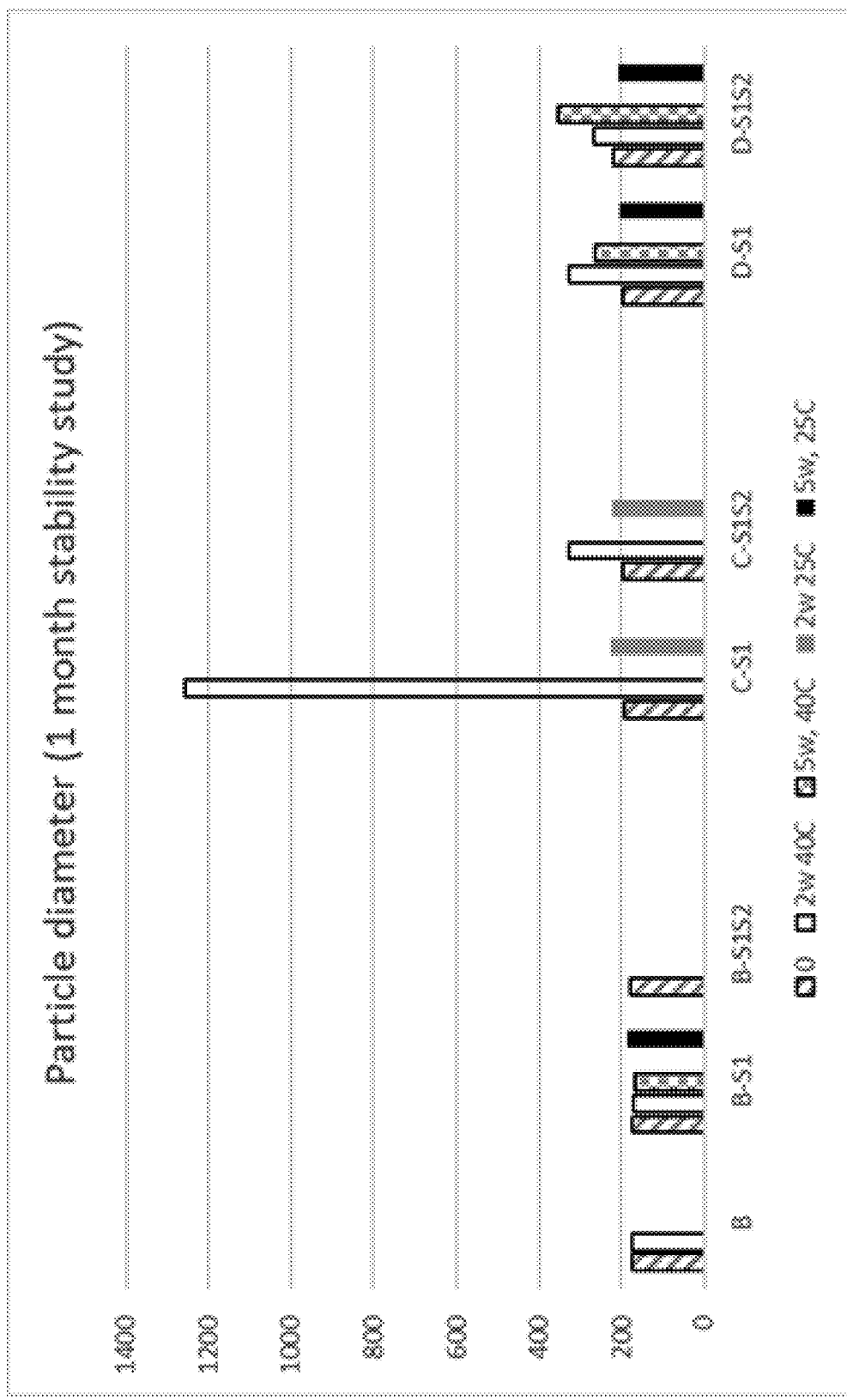
FIG. 11 is a bar graph illustrating experimental results describing stability over time.
Figure 12:
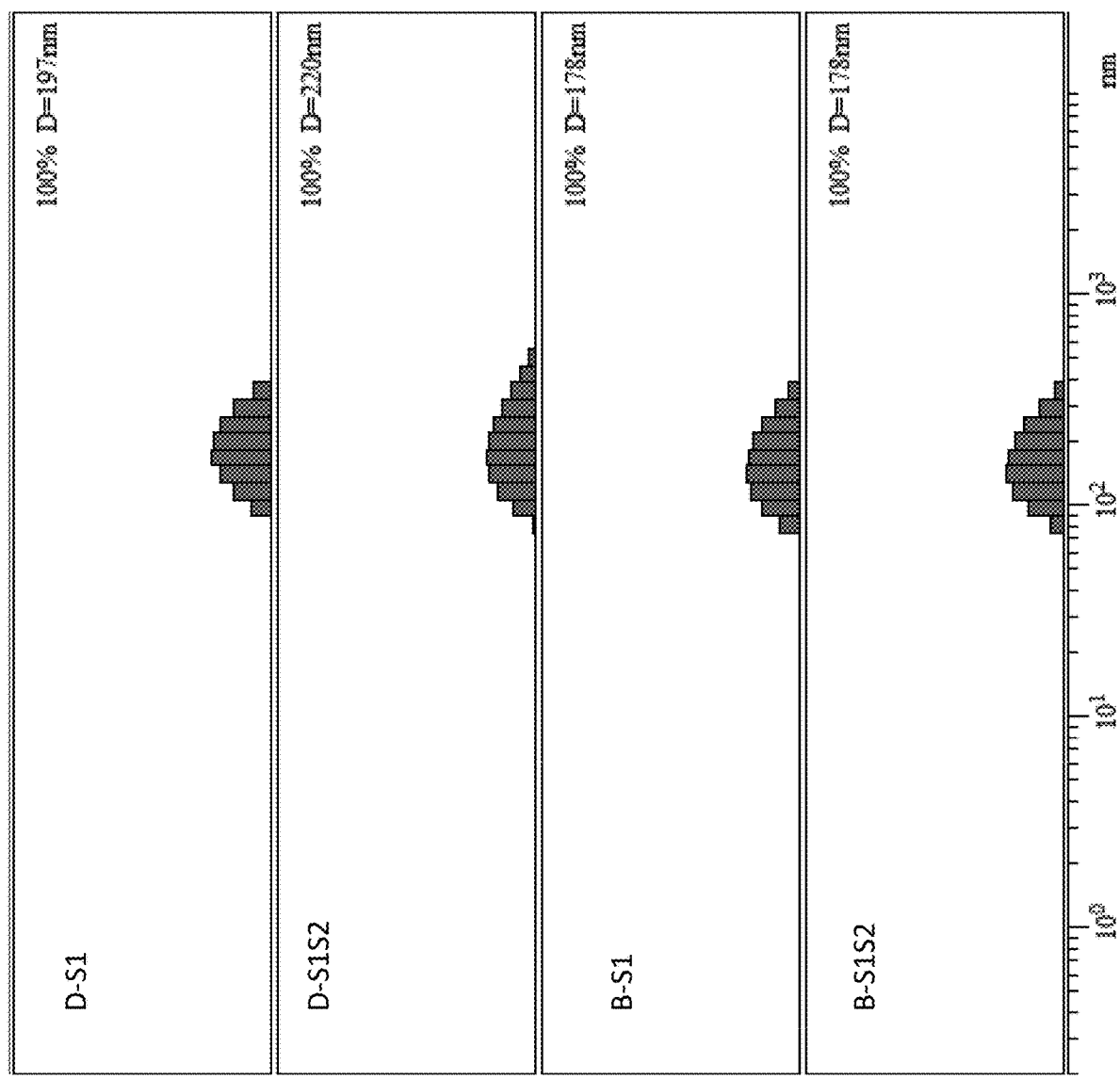
FIGS. 12 and 13 are histograms illustrating experimental results describing stability over time.
Figure 13:
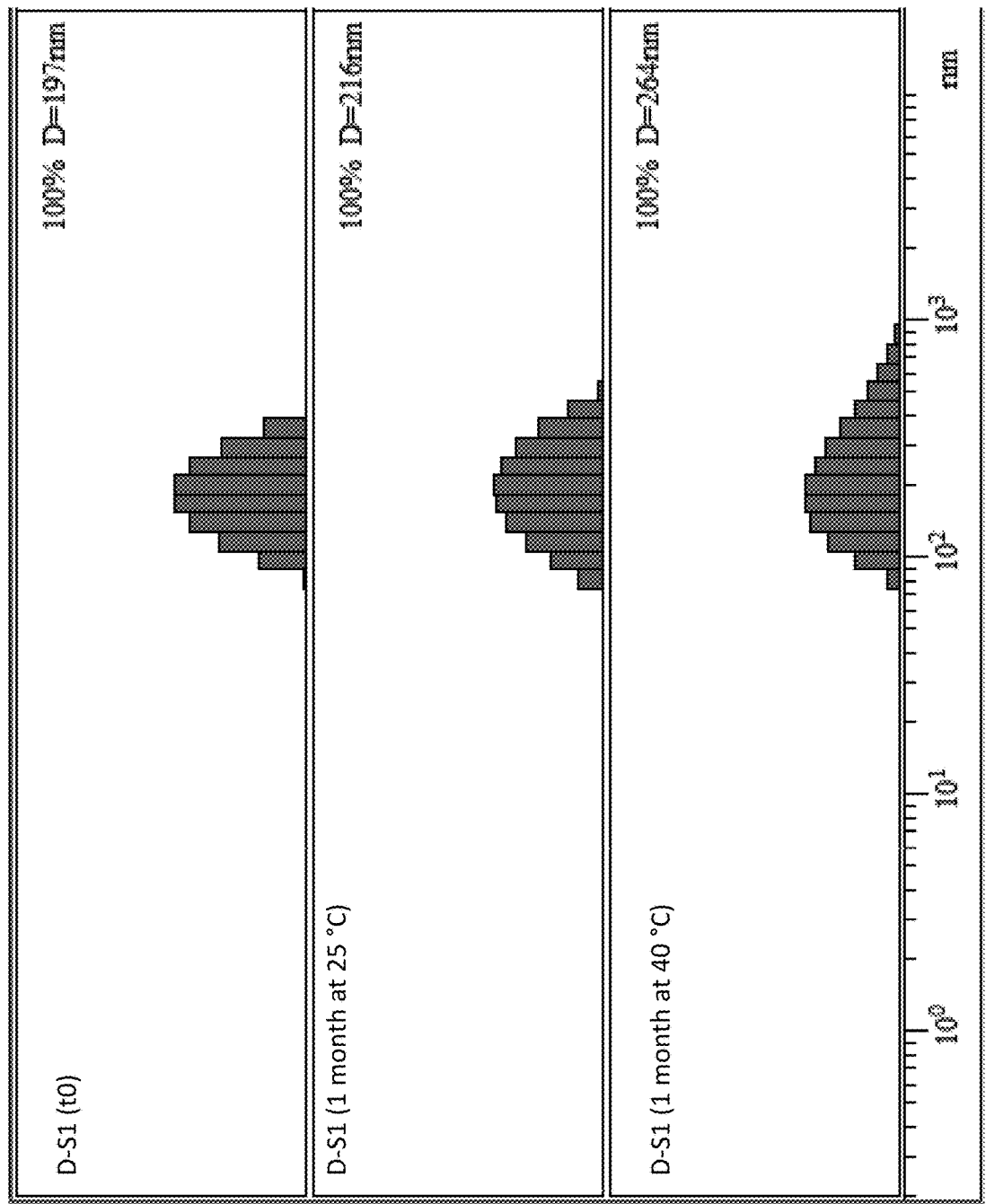

Referring now to FIG. 7, a bar graph illustrates experimental results comparing IgG immune response (vertical axis) measured from sera extracted from mice vaccinated using embodiments of disclosed vaccine in which the antigen was an S1 protein without S2 protein component. ELISA was performed with S1-immobilized plates. Naïve samples (unvaccinated) were compared to sera samples from mice vaccinated with four other formulations of a solution of S1 glycoproteins, denoted "S1,", a vaccine formulated using a lipid blend that has not be lyophilized, which was mixed with antigens (in this case S1), which process is referred to in the graphs as "A-S1" as described above in reference to FIG. 6, a formulation of lipid blend lyophilized and reconstituted with S1 spike proteins, referred to in the graphs as "B-S1" as described above in reference to FIG. 6, and a formulation of freeze-dried lipid blend reconstituted with spike protein (S1) solution, then freeze-dried again, and reconstituted a second time, denoted formulation "D-S1" as described above in reference to FIG. 6. As shown in FIG. 6, A-S1, B-S1, and D-S1 all formulations significantly outperformed S1 alone and control resulting in a statistically significant increase in S1-neutralizing antibody response, while B-S1 outperformed A-S1 and D-S1 by a significant margin.

Referring now to FIG. 8, a bar graph illustrates experimental results comparing immune response (vertical axis) measured for sera from mice vaccinated using embodiments of disclosed vaccine in which the antigen was an S1 with no S2, placed on plates coated with S1S2. As before naïve control, S1, A-S1, B-S1, and D-S1 solutions were used. As illustrated in FIG. 7, all three vaccines were immunogenic.

Referring now to FIG. 9, a bar graph illustrates experimental results comparing immune response (vertical axis) measured for blood from mice vaccinated using embodiments of disclosed vaccine in which the antigen was an S1S2 vaccine on a plate coated with S1. Formulations included "S1S2," which was a solution of S1S2 alone, "A-S1S2," prepared as described above for A-S1, but with S1S2 spike proteins instead of S1 alone, "B-S1S2," prepared as described above for B-S1, but with S1S2 spike proteins instead of S1 alone, and "D-S1S2," prepared as described above for D-S1, but with S1S2 spike proteins instead of S1 alone. All formulations were significantly more immunogenic than control, with B-S1S2 far outperforming others.

Referring now to FIG. 10, a bar graph illustrates experimental results comparing immune response (vertical axis) measured for blood from mice vaccinated using embodiments of disclosed vaccine in which the antigen was an S1S2 vaccine on a plate coated with S1S2. Formulations included S1S2, A-S1S2, B-S1S2, and D-S1S2. All formulations were significantly more immunogenic than control, with D-S1S2 and A-S1S2 outperforming B-S1S2.

Referring now to FIG. 11, a graph showing experimental results of stability assessments at one month as described above is provided. Formulations C-S1 and C-S1S2 were not lyophilized. Formulations B-S1 and B-S1S2, which have been described above, were reconstituted, with antigens, as described above at a time of stability assessment. Formulations D-S1 and D-S1S2 were reconstituted at a time of assessment as well. As illustrated in FIG. 11 and shown in Table 1 with respect to particle size, Lyophilized vaccines (D-S1 and D-S1S2) and lyophilized adjuvant (B) were stable at 25 C for at least 5 weeks, and at 40 C for at least 2 weeks. When lyophilized adjuvant B was reconstituted at t0 with S1 protein, it resulted in a vaccine particle with a size that did not change significantly if the adjuvant was stored for 5 weeks at 25 or for 2 weeks at 40 C. This would indicate that the liposomal adjuvant B is stable at 25 for at least 5 weeks and at 40 C for at least 2 weeks. FIGS. 12 and 13 show representative histograms for effect of temperature on B and D formulations, respectively. Lyophilization increased vaccine stability at 25 C and 40 C. Liquid vaccines C-S1 and C-S1S2 were not stable at either temperature for 2 weeks.

TABLE 1

| Vaccine | t0 | 2 w 25 C. | 5 w, 25 C. | 2 w 40 C. | 5 w, 40 C. |
| --- | --- | --- | --- | --- | --- |
| B | 176 ± 3 | | | 173 ± 6 | |
| B-S1 | 176 ± 3 | — | 186 ± 6 | 170 ± 2 | 166 ± 3 |
| B-S1S2 | 178 ± 2 | — | — | — | — |
| C-S1 | 193 ± 4 | 225 ± 5 | — | 1,257 ± 266 | — |
| C-S1S2 | 196 ± 3 | 221 ± 3 | — | 326 ± 30 | — |
| D-S1 | 198 ± 4 | — | 203 ± 16 | 326 ± 74 | 262 ± 9 |
| D-S1S2 | 218 ± 7 | | 209 ± 5 | 269 ± 22 | 355 ± 52 |

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve embodiments according to this disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A method of manufacturing an immunogenic composition forming a vaccine, the method comprising:
    forming a nanoparticle adjuvant, wherein:
        the adjuvant comprises at least a nanoparticle, wherein the at least a nanoparticle comprises a lipid layer exterior including at least one lipid, wherein the lipid layer exterior further comprises dipalmitoyl phosphatidylcholine (DPPC), dioleoylphosphatidylcholine (DOPC), cholesterol, and a primary alkyl amine including a positively charged amino group head and at least a carbon tail and wherein the DPPC:DOPC:cholesterol:alkyl amine molar ratio is 40:20-30:20:10-30;
    providing an antigen, the antigen comprising a spike protein from SARS-CoV-2; and
    combining the antigen with the nanoparticle adjuvant, wherein combining the antigen with the nanoparticle adjuvant comprises:
        lyophilizing the nanoparticle adjuvant;
        combining the antigen with a buffer to form a suspension; and
        reconstituting the nanoparticle adjuvant with the suspension.

2. The method of claim 1, wherein the lipid layer is positively charged.

3. The method of claim 1, wherein each nanoparticle includes a liposome.

4. The method of claim 1, wherein the spike protein includes an S1 protein.

5. The method of claim 1, wherein the spike protein includes an S1S2 protein.

6. The method of claim 1 further comprising adding at least one lyoprotectant to the combined adjuvant and antigen.

7. The method of claim 1, wherein the plurality of spike proteins further comprises recombinant proteins.

8. The method of claim 1, wherein the primary alkyl amine includes stearylamine.

9. The method of claim 1, wherein the primary alkyl amine comprises a branched alkyl amine.

10. The method of claim 1, wherein the antigen has an electric charge with a first polarity; and
    the lipid layer exterior has an electric charge with a second polarity, wherein the first polarity differs from the second polarity.

11. The method of claim 1, wherein the antigen is absorbed in the surface of the lipid layer.

12. The method of claim 1, wherein the spike protein includes an S2 protein embedded in the lipid layer and an S1 protein projecting from the lipid layer.

13. The method of claim 3, further comprising trapping the spike protein in an aqueous compartment of the liposome.

14. The method of claim 1, wherein the lipid layer exterior comprises non-phospholipids lipids.

15. The method of claim 14, wherein the non-phospholipids lipids are combined with polyethylene glycols.

16. The method of claim 1, wherein each of the at least a nanoparticle has a diameter between 1000 and 2000 nanometers.

17. The method of claim 1, wherein the lipid layer further comprises a lipid bilayer, and wherein the spike protein is entrapped within the lipid bilayer.

18. The method of claim 1, wherein the lipid layer exterior includes cholesterol in an amount ranging from 20 mol % to 30 mol %.

19. The method of claim 1, wherein the antigen includes glycoprotein.

* * * * *